(12) United States Patent
Katsura et al.

(10) Patent No.: US 8,288,579 B2
(45) Date of Patent: Oct. 16, 2012

(54) METHOD FOR PRODUCING N-METHACRYLOYL-4-CYANO-3-TRIFLUOROMETHYLANILINE

(75) Inventors: Tadashi Katsura, Toyonaka (JP); Tadashi Mizuno, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 55 days.

(21) Appl. No.: 12/675,834

(22) PCT Filed: Sep. 2, 2008

(86) PCT No.: PCT/JP2008/066143
§ 371 (c)(1),
(2), (4) Date: Mar. 1, 2010

(87) PCT Pub. No.: WO2009/034936
PCT Pub. Date: Mar. 19, 2009

(65) Prior Publication Data
US 2010/0249446 A1   Sep. 30, 2010

(30) Foreign Application Priority Data
Sep. 12, 2007  (JP) .................................. 2007-236507

(51) Int. Cl.
*C07C 255/50*  (2006.01)
(52) U.S. Cl. ....................................... 558/413; 558/414
(58) Field of Classification Search ........................ None
See application file for complete search history.

(56) References Cited

FOREIGN PATENT DOCUMENTS

| | | |
|---|---|---|
| EP | 0 365 763 A1 | 5/1990 |
| JP | 02-174749 A | 7/1990 |
| JP | 2005-060302 A | 3/2005 |

OTHER PUBLICATIONS

Tucker et al. J. Med. Chem. (1998), 31, pp. 954-959.*
Notification and International Preliminary Report on Patentability and Translation of the Written Opinion received in the corresponding International Patent Application No. PCT/JP2008/066143.
Friedman, et al. "Dimethylformamide as a Useful Solvent in Preparing Nitriles from Aryl Halides and Cuprous Cyanide; Improved Isolation Techniques", Journal of Organic Chemistry, Jul. 1961, vol. 26, pp. 2522-2524.
International Search Report in PCT/JP2008/066143 dated Nov. 25, 2008.
The Chemical Society of Japan, 5th edition, "Jikken Kagaku Koza 1-Kisohen I Jikken Joho no Kiso-", Maruzen Co., Ltd., 2003 Nen, pp. 163-167.

* cited by examiner

*Primary Examiner* — Kamal Saeed
*Assistant Examiner* — Nyeemah A Grazier
(74) *Attorney, Agent, or Firm* — Foley & Lardner LLP

(57) ABSTRACT

A method for producing N-methacryloyl-4-cyano-3-trifluoromethylaniline, wherein 4-cyano-3-trifluoromethylaniline is crystallized from a mixed solvent of methanol and water, and the obtained 4-cyano-3-trifluoromethylaniline is reacted with methacryloyl chloride improved separation property even in industrial production in a large scale.

3 Claims, No Drawings

METHOD FOR PRODUCING N-METHACRYLOYL-4-CYANO-3-TRIFLUOROMETHYLANILINE

TECHNICAL FIELD

The present invention relates to a method for producing N-methacryloyl-4-cyano-3-trifluoromethylaniline that is a raw material for producing bicalutamide.

BACKGROUND ART

Bicalutamide represented by the formula (I):

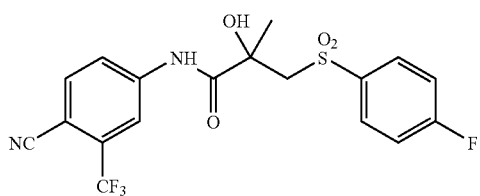

(I)

is useful as a compound having an antiandrogenic activity.

Regarding a production method of bicalutamide, various methods have been known in JP-2005-60302A and the like, and N-methacryloyl-4-cyano-3-trifluoromethylaniline which is obtainable from 4-cyano-3-trifluoromethylaniline represented by the formula (II):

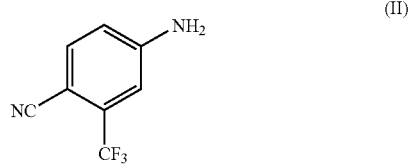

(II)

is generally used as a raw material.

For example, JP-2005-60302A discloses a method for producing N-methacryloyl-4-cyano-3-trifluoromethylaniline by reacting 4-cyano-3-trifluoromethylaniline with methacryloyl chloride. Further, EP-365763A discloses a preparation method of crystallizing 4-cyano-3-trifluoromethylaniline in ethanol/water.

When, N-methacryloyl-4-cyano-3-trifluoromethylaniline was produced from 4-cyano-3-trifluoromethylaniline industrially in a large scale according to the method described in JP-2005-60302A, a defect in a liquid separation property was observed in steps of extracting N-methacryloyl-4-cyano-3-trifluoromethylaniline from a reaction solution and washing the extract. This defect in the liquid separation property was not easily improved with change in extraction and washing methods.

DISCLOSURE OF THE INVENTION

The present invention provides a method suitable for producing N-methacryloyl-4-cyano-3-trifluoromethylaniline from 4-cyano-3-trifluoromethylaniline in an industrial scale.

The present invention directs to a method for producing N-methacryloyl-4-cyano-3-trifluoromethylaniline, wherein 4-cyano-3-trifluoromethylaniline is crystallized from a mixed solvent of methanol and water, and the obtained 4-cyano-3-trifluoromethylaniline is reacted with methacryloyl chloride. The invention makes it possible to easily separate N-methacryloyl-4-cyano-3-trifluoromethylaniline from a reaction solution, and thus, the production method was improved.

4-Cyano-3-trifluoromethylaniline can be prepared according to the description of EP-365763A. A commercially available product of 4-cyano-3-trifluoromethylaniline can also be used.

4-Cyano-3-trifluoromethylaniline is dissolved in a mixture of methanol and water with heating and then cooled, thereby depositing a crystal.

Per 1 kg of 4-cyano-3-trifluoromethylaniline, methanol is generally used at the rate of 5 to 7 L, and preferably 5.5 to 6.5 L, and water is used at the rate of 3 to 5 L, and preferably 3.5 to 4.5 L.

When 4-cyano-3-trifluoromethylaniline is dissolved in a mixture of methanol and water, the mixture is generally heated to a temperature within the range from 65 to 80° C., and when a crystal is to be deposited, the mixture is generally cooled to a temperature within the range from 45 to 65° C. In addition, crystallization can also be performed by a method for preparing a mixed solvent by dissolving 4-cyano-3-trifluoromethylaniline in methanol and adding water thereto.

When 4-cyano-3-trifluoromethylaniline is to be crystallized from a mixed solvent of methanol and water, a 4-cyano-3-trifluoromethylaniline solution is preferably treated with activated carbon. As activated carbon, for example, a commercially available product such as Shirasagi A-1 (made by Japan EnviroChemicals, Ltd.) can be used. A treatment with activated carbon can be generally performed at a temperature within the range from 65 to 80° C., and the 4-cyano-3-trifluoromethylaniline solution is added with activated carbon and stirred, and activated carbon is removed by filtration. Activated carbon is used generally at the rate of 0.03 to 0.3 part by weight per 1 part by weight of 4-cyano-3-trifluoromethylaniline.

As methacryloyl chloride to be reacted with 4-cyano-3-trifluoromethylaniline, a commercially available product may be used as it is, and it is also possible to prepare methacryloyl chloride to be used from methacrylic acid and a chlorinating agent such as thionyl chloride, phosphorus oxychloride, or oxalyl chloride.

When methacryloyl chloride is prepared, an amount of a chlorinating agent to be used is 1 to 1.2 equivalent weight, and preferably 1 to 1.1 equivalent weight based on 1 equivalent weight of methacrylic acid. As a solvent used for preparation of methacryloyl chloride, N,N-dimethylacetamide, N-methylpyrrolidone, and the like are preferable. The reaction temperature for preparing methacryloyl chloride is generally −20 to 5° C., and preferably −12 to 2° C., and the reaction time is generally 0.5 to 4 hours, and preferably 1 to 2 hours.

In a method of preparing methacryloyl chloride, a reaction may be performed by adding 4-cyano-3-trifluoromethylaniline to a system for preparing methacryloyl chloride. In this case, N-methacryloyl-4-cyano-3-trifluoromethylaniline can be produced in one pot and thus the method is industrially preferable. In addition, in order to produce N-methacryloyl-4-cyano-3-trifluoromethylaniline in one pot, a reaction may be performed wherein methacryloyl chloride is prepared in the presence of a polymerization inhibitor described later such as dibutylhydroxytoluene and 4-cyano-3-trifluoromethylaniline is added thereto.

Examples of a solvent for a reaction of 4-cyano-3-trifluoromethylaniline with methacryloyl chloride include N,N-dimethylacetamide and N-methylpyrrolidone, and N,N-dimethylacetamide is preferable.

The amount of the reaction solvent is not particularly limited, and is preferably within the range from 2 to 5 parts by weight, and more preferably within the range from 3.5 to 4.5 parts by weight based on 1 part by weight of 4-cyano-3-trifluoromethylaniline. When the amount of the reaction solvent to be used is less than 2 parts by weight based on 1 part by weight of 4-cyano-3-trifluoromethylaniline, there is a fear of causing a defect in stirring a reaction solution, and when it is more than 5 parts by weight, the reaction speed tends to decrease.

The reaction temperature of 4-cyano-3-trifluoromethylaniline and methacryloyl chloride is generally −15 to 10° C., and preferably −12 to 2° C. The reaction time of 4-cyano-3-trifluoromethylaniline and methacryloyl chloride is generally 0.5 to 4 hours, and preferably 1 to 2 hours. In addition, when methacryloyl chloride is dropped to 4-cyano-3-trifluoromethylaniline, the reaction time means the time after completion of the dropping.

The reaction of 4-cyano-3-trifluoromethylaniline with methacryloyl chloride is preferably performed in the presence of a polymerization inhibitor such as dibutylhydroxytoluene or dibutylhydroxyanisole from the viewpoint of suppression of side reactions. The polymerization inhibitor is added preferably within the range from 0.0001 to 0.01 part by weight based on 1 part by weight of 4-cyano-3-trifluoromethylaniline.

The reaction mixture is generally subjected to post treatments such as organic solvent extraction, washing, and solvent distillation to thus isolate N-methacryloyl-4-cyano-3-trifluoromethylaniline, which can be further purified by a general method such as recrystallization or chromatography.

To the reaction mixture, an aqueous alkaline solution for neutralizing an acid, preferably an aqueous sodium carbonate solution (in particular, an aqueous 16% sodium carbonate solution) is generally added, and the mixture is extracted with an organic solvent such as ethyl acetate. The temperature in adding an aqueous alkaline solution is preferably 0 to 25° C. In general, an organic solvent is separated at 20 to 30° C.

The organic layer is generally washed with saline water (preferably 15% saline water) 1 to 4 times, preferably 2 to 3 times. Separation of the organic layer and saline water is performed generally at 50 to 70° C., and preferably at 55 to 65° C.

According to the present invention, a liquid separation property is improved when N-methacryloyl-4-cyano-3-trifluoromethylaniline is produced industrially in a large scale. Improvement in the liquid separation property can be confirmed by, for example, a technique in which a mixed solution of an organic layer and an aqueous layer is poured in a 1 L-measuring cylinder, the time (T seconds) until the interface between the organic layer and the aqueous layer is clearly confirmed is measured, the height (Hm) of the liquid in the measuring cylinder is measured, and then, the liquid separation speed is calculated by the equation:

Liquid separation speed (m/hr)=(Hm×3600 (sec))/T (sec).

After liquid separation, when the organic layer is an ethyl acetate layer, the layer is desirably concentrated at 80° C. or less, preferably 40 to 80° C., and more preferably 50 to 60° C. at 30 to 60 kPa, and preferably 30 to 40 kPa.

The present invention will be more specifically described by way of examples below.

EXAMPLES

Example 1

A reaction container was charged with 50 kg of commercially available 4-cyano-3-trifluoromethylaniline (LC surface percentage (hereinafter also abbreviated as surface percentage): 98.34%), 285 L of methanol, 190 L of water, and 5 kg of activated carbon, and the temperature was increased to 72° C. After the mixture was stirred at 72 to 75° C. for 30 minutes, activated carbon was removed by filtration at the same temperature and further washed with a mixed solvent of 15 L of methanol and 10 L of water. The filtrate and the washing solution were combined and cooled to 54° C. and seeded at the same temperature with 25 g of 4-cyano-3-trifluoromethylaniline that had been previously purified, and the resultant mixture was cooled to 45° C., and thereafter stirred at the same temperature for 30 minutes. Then, the mixture was cooled to 20° C. and stirred at the same temperature for 1 hour. Crystals of 4-cyano-3-trifluoromethylaniline were separated by filtration and washed with a mixed solvent of 45 L of methanol and 30 L of water to give 41.4 kg of wet crystals. The wet crystals were dried under reduced pressure to obtain 36.5 kg of crystals of 4-cyano-3-trifluoromethylaniline. The LC surface percentage was 99.85%, and the yield was 73%.

A reaction container was charged with 64.9 kg of dimethylacetamide, 22.4 kg of methacrylic acid, and 40 g of dibutylhydroxytoluene, and the temperature was reduced to −5° C. Thionyl chloride in an amount of 31.0 kg was dropped thereto at −8.1 to −3.4° C. over 3.7 hours, and the mixture was kept at −8.2 to −6.5° C. for 1 hour. 4-Cyano-3-trifluoromethylaniline obtained as described above in an amount of 36.4 kg was dissolved in 75.1 kg of N,N-dimethylacetamide and dropped into the reaction container at −8.2 to −3.3° C. over 4.8 hours. The container for dropping 4-cyano-3-trifluoromethylaniline was washed with 10.2 kg of N,N-dimethylacetamide, the washing liquid was added to the reaction solution, and the solution was kept at −4.3 to −2.4° C. for 1 hour. After completion of the reaction, the reaction solution was dropped to a mixed solution of 279.0 kg of ethyl acetate and 255.0 kg of water at 20° C. or less. The container for dropping was washed with 17.1 kg of N,N-dimethylacetamide, and the washing liquid was added to the mixed solution. Thereto was added 343.3 kg of an aqueous 16% sodium carbonate solution to adjust the pH to 7.0, and the resultant solution was stirred for 30 minutes and made to stand still for 30 minutes, followed by liquid separation. The liquid separation speed was 3.5 m/hr. The organic layer was added with 578.6 kg of 15% saline water to set the internal temperature to 60° C., and the mixture was stirred for 30 minutes and made to stand still for 30 minutes, followed by liquid separation. The liquid separation speed was 19.4 m/hr. The organic layer was added with 578.6 kg of 15% saline water to set the internal temperature to 60° C., and the mixture was stirred for 30 minutes and then made to stand still for 30 minutes, followed by liquid separation. The liquid separation speed was 16.2 m/hr. The organic layer was further added with 578.6 kg of 15% saline water to set the internal temperature to 60° C., and the mixture was stirred for 30 minutes and made to stand still for 30 minutes, followed by liquid separation. The liquid separation speed was 20.5 m/hr.

Then, the organic layer was charged with 201.4 kg of chlorobenzene, and ethyl acetate and chlorobenzene were distilled out in an amount of 220.5 kg by vacuum concentration. 564.1 kg of chlorobenzene, 1.8 kg of activated carbon and 4.9 kg of γ-alumina were charged and the mixture was stirred at 75° C. for 30 minutes. Then, the alumina and activated carbon were separated by filtration at the same temperature and washed with 40.3 kg of chlorobenzene. The filtrate and the washing solution were combined, and 535.0 kg of chlorobenzene was distilled out by vacuum concentration, and then the mixture was cooled to 20° C. and stirred at 15 to 20° C. for 1 hour. Crystals were separated by filtration and washed with 120.9 kg of a chlorobenzene solution dissolved with 0.55 kg of dibutylhydroxytoluene to give 49.7 kg of wet crystals. After drying the crystals under reduced pressure, 43.4 kg of N-methacryloyl-4-cyano-3-trifluoromethylaniline was obtained. The LC surface percentage was 99.9%, and the yield was 87.3%.

Reference Example 1

A reaction container was charged with 70 g of commercially available 4-cyano-3-trifluoromethylaniline (LC surface percentage: 99.39%) and 350 mL of ethanol, and the temperature was increased to 72° C. After the mixture was stirred at 72 to 75° C. for 30 minutes, insoluble matters were removed by filtration at the same temperature and the mixture was further washed with 10 mL of ethanol. The filtrate thus obtained was cooled to 57° C., and 360 mL of water was dropped at the same temperature over about 4 hours. 30 mg of 4-cyano-3-trifluoromethylaniline that had been previously purified was seeded thereto and the resultant mixture was cooled to 45° C., and thereafter stirred at the same temperature for 30 minutes. Then, the mixture was cooled to 25° C. and stirred at the same temperature for 1 hour. Crystals were separated by filtration and washed with a mixed solvent of 56 mL of ethanol and 56 mL of water to give 83.81 g of wet crystals. The wet crystals were dried under reduced pressure to obtain 50.61 g of 4-cyano-3-trifluoromethylaniline. The LC surface percentage was 99.90%, and the yield was 72.3%.

A reaction container was charged with 68 mL of N,N-dimethylacetamide, 22.1 g of methacrylic acid, and 38 mg of dibutylhydroxytoluene, and the temperature was reduced to −5° C. Thionyl chloride in an amount of 30.6 g was dropped thereto at −3.8 to 0.3° C. over 50 minutes, and the mixture was kept at −4.0 to −0.8° C. for 30 minutes. A solution obtained by dissolving 36.0 g of 4-cyano-3-trifluoromethylaniline obtained as described above in 79 mL of N,N-dimethylacetamide was dropped into the reaction container at −5.3 to 0° C. over 65 minutes. The container for dropping was washed with 11 mL of N,N-dimethylacetamide, the washing liquid was added to the reaction solution, and the solution was kept at −5.3 to 0° C. for 1 hour. After completion of the reaction, the obtained reaction solution was dropped to a mixed solution of 306 mL of ethyl acetate and 252 mL of water at 20° C. or less. The solution was washed with 18 mL of N,N-dimethylacetamide and the washing solution and the mixed solution were combined, and 378.1 g of an aqueous 16% sodium carbonate solution was added to the solution to adjust the pH to 7.1. The resultant solution was stirred for 30 minutes and made to stand still for 30 minutes, followed by liquid separation. The liquid separation speed calculated in the same manner as in Example 1 was 1.7 m/hr. The organic layer was added with 571.8 g of 15% saline water to set the internal temperature to 60° C. The resultant solution was stirred for 30 minutes and made to stand still for 30 minutes, followed by liquid separation. The liquid separation speed calculated in the same manner as in Example 1 was 3.9 m/hr. The organic layer was added with 571.8 g of 15% saline water to set the internal temperature to 60° C. The resultant solution was stirred for 30 minutes and made to stand still for 30 minutes, followed by liquid separation. The liquid separation speed calculated in the same manner as in Example 1 was 3.6 m/hr. The organic layer was further added with 571.8 g of 15% saline water to set the internal temperature to 60° C. The resultant solution was stirred for 30 minutes and then made to stand still for 30 minutes, followed by liquid separation. The liquid separation speed calculated in the same manner as in Example 1 was 3.0 m/hr.

Then, the organic layer was charged with 180 mL of chlorobenzene, and ethyl acetate and chlorobenzene were distilled out in an amount of 222.3 g by vacuum concentration. Next, 504 mL of chlorobenzene, 1.8 g of activated carbon and 4.9 g of γ-alumina were charged and the mixture was stirred at 75° C. for 30 minutes. The alumina and activated carbon were separated by filtration at the same temperature and washed with 36 mL of chlorobenzene. The filtrate and the washing solution were combined, and 545.5 g of chlorobenzene was distilled out by vacuum concentration, and then the mixture was cooled to 20° C. and stirred at 15 to 20° C. for 2 hours. Crystal were separated by filtration and washed with 108 mL of a chlorobenzene solution dissolved with 0.45 g of dibutylhydroxytoluene to give 48.94 g of wet crystals. After drying the crystal under reduced pressure, 45.27 g of crystals of N-methacryloyl-4-cyano-3-trifluoromethylaniline was obtained. The LC surface percentage was 99.92%, and the yield was 92.1%.

Reference Example 2

A reaction container was charged with 85.5 kg of N,N-dimethylacetamide, 29.5 kg of methacrylic acid, and 0.05 kg of dibutylhydroxytoluene, and the temperature was reduced to −5° C. Thionyl chloride in an amount of 40.8 kg was dropped thereto at −4.1 to −3.9° C. over 4.0 hours, and the mixture was kept at −6.9 to −4.1° C. for 1 hour. A solution obtained by dissolving 48.0 kg of commercially available 4-cyano-3-trifluoromethylaniline (LC surface percentage: 99.39%) in 98.9 kg of N,N-dimethylacetamide was dropped into the reaction container at −6.9 to −3.0° C. over 6.1 hours. The container for dropping was washed with 13.5 kg of N,N-dimethylacetamide, the washing liquid was added to the reaction solution, and the solution was kept at −4.8 to −3.0° C. for 1 hour. After completion of the reaction, the reaction solution was dropped to a mixed solution of 367.6 kg of ethyl acetate and 336.0 kg of water at 20° C. or less. The container was washed with 22.5 kg of N,N-dimethylacetamide, and the washing solution was combined with the mixed solution. Thereto was added 477.6 kg of an aqueous 16% sodium carbonate solution to adjust the pH to 7.0, and the resultant solution was stirred for 30 minutes and made to stand still for 30 minutes, followed by liquid separation. The liquid separation speed calculated in the same manner as in Example 1 was 0.7 m/hr. The organic layer was added with 762.4 kg of 15% saline water to set the internal temperature to 60° C. The resultant solution was stirred for 30 minutes and made to stand still for 30 minutes, followed by liquid separation. The liquid separation speed calculated in the same manner as in Example 1 was 0.8 m/hr. The organic layer was added with 762.4 kg of 15% saline water to set the internal temperature to 60° C. The resultant solution was stirred for 30 minutes and then made to stand still for 30 minutes, followed by liquid separation. The liquid separation speed calculated in the same manner as in Example 1 was 1.2 m/hr. The organic layer was further added with 762.4 kg of 15% saline water to set the internal temperature to 60° C. The resultant solution was stirred for 30 minutes and made to stand still for 30 minutes, followed by liquid separation. The liquid separation speed calculated in the same manner as in Example 1 was 4.3 m/hr.

The organic layer was charged with 265.4 kg of chlorobenzene, and ethyl acetate and chlorobenzene were distilled out in an amount of 295.0 kg by vacuum concentration. 743.2 kg of chlorobenzene, 2.4 kg of activated carbon and 6.5 kg of γ-alumina were charged and the mixture was stirred at 75° C. for 30 minutes. Then, the alumina and activated carbon were separated by filtration at the same temperature and washed with 53.1 kg of chlorobenzene. The filtrate and the washing solution were combined, and 697.2 kg of chlorobenzene was distilled out by vacuum concentration. The residual solution was then cooled to 20° C. and stirred at 15 to 20° C. for 1 hour. Crystals were separated by filtration and washed with 159.3 kg of a chlorobenzene solution dissolved with 0.73 kg of dibutylhydroxytoluene to give 68.9 kg of wet crystals. After drying the crystals under reduced pressure, 57.9 kg of N-methacryloyl-4-cyano-3-trifluoromethylaniline was obtained. The LC surface percentage was 99.95%, and the yield was 88.3%.

Reference Example 3

A reaction container was charged with 85.5 kg of N,N-dimethylacetamide, 29.5 kg of methacrylic acid, and 0.05 kg of dibutylhydroxytoluene, and the temperature was reduced to −5° C. Thionyl chloride in an amount of 40.8 kg was dropped thereto at −4.3 to −2.3° C. over 4.2 hours, and the mixture was kept at −7.6 to −2.3° C. for 1 hour. A solution obtained by dissolving 48.0 kg of commercially available 4-cyano-3-trifluoromethylaniline (LC surface percentage: 99.39%) in 98.9 kg of N,N-dimethylacetamide was dropped into the reaction container at −7.6 to −0.8° C. over 5.9 hours. The container was washed with 13.5 kg of N,N-dimethylacetamide, the washing liquid was added to the reaction solution, and the solution was kept at −2.0 to −0.8° C. for 1 hour. After completion of the reaction, the reaction solution was dropped to a mixed solution of 367.6 kg of ethyl acetate and 336.0 kg of water at 20° C. or less. The container for dropping was washed with 22.5 kg of N,N-dimethylacetamide and the washing liquid was added to the reaction solution. Thereto was added 489.1 kg of an aqueous 16% sodium carbonate solution to adjust the pH to 7.1. The resultant solution was stirred for 30 minutes and made to stand still for 30 minutes, followed by liquid separation. The liquid separation speed calculated in the same manner as in Example 1 was 0.62 m/hr. The organic layer was added with 762.4 kg of 15% saline water to set the internal temperature to 60° C. The resultant solution was stirred for 30 minutes and made to stand still for 30 minutes, followed by liquid separation. The liquid separation speed calculated in the same manner as in Example 1 was 0.62 m/hr. The organic layer was added with 762.4 kg of 15% saline water to set the internal temperature to 60° C. The resultant solution was stirred for 30 minutes and then made to stand still for 30 minutes, followed by liquid separation. The liquid separation speed calculated in the same manner as in Example 1 was 0.5 m/hr. The organic layer was added with 762.4 kg of 15% saline water to set the internal temperature to 60° C. The resultant solution was stirred for 30 minutes and made to stand still for 30 minutes, followed by liquid separation. The liquid separation speed calculated in the same manner as in Example 1 was 0.75 m/hr. The organic layer was further added with 762.4 kg of 15% saline water to set the internal temperature to 60° C. The resultant solution was stirred for 30 minutes and then made to stand still for 30 minutes, followed by liquid separation. The liquid separation speed calculated in the same manner as in Example 1 was 1.0 m/hr.

Then, the organic layer was charged with 265.4 kg of chlorobenzene, and ethyl acetate and chlorobenzene were distilled out in an amount of 309.2 kg by vacuum concentration. Next, 755.8 kg of chlorobenzene, 2.4 kg of activated carbon and 6.5 kg of γ-alumina were charged and the mixture was stirred at 75° C. for 30 minutes. Then, the alumina and activated carbon were separated by filtration at the same temperature and washed with 53.1 kg of chlorobenzene. By vacuum concentration, 684.1 kg of chlorobenzene was distilled out. The residual solution was cooled to 20° C. and stirred at 15 to 20° C. for 1 hour. Crystals were separated by filtration and washed with 159.3 kg of a chlorobenzene solution dissolved with 0.73 kg of dibutylhydroxytoluene to give 67.0 kg of wet crystals. After drying the crystals under reduced pressure, 58.6 kg of N-methacryloyl-4-cyano-3-trifluoromethylaniline was obtained. The LC surface percentage was 99.95%, and the yield was 89.4%.

Reference Example 4

A reaction container was charged with 85.5 kg of N,N-dimethylacetamide, 29.5 kg of methacrylic acid, and 0.05 kg of dibutylhydroxytoluene, and the temperature was reduced to −5° C. Thionyl chloride in an amount of 40.8 kg was dropped thereto at −6.4 to −3.2° C. over 3.8 hours, and the mixture was kept at −9.1 to −4.2° C. for 1 hour. A solution obtained by dissolving 48.0 kg of commercially available 4-cyano-3-trifluoromethylaniline (LC surface percentage: 99.39%) in 98.9 kg of N,N-dimethylacetamide was dropped into the reaction container at −9.2 to −0.9° C. over 5.7 hours. The container was washed with 13.5 kg of N,N-dimethylacetamide, the washing liquid was added to the reaction solution, and the solution was kept at 0.2 to 1.7° C. for 2 hours. After completion of the reaction, the reaction solution was dropped to a mixed solution of 310.0 kg of ethyl acetate, 91.0 kg of sodium carbonate, and 816.0 kg of water at 20° C. or less. The container was washed with 22.5 kg of N,N-dimethylacetamide, and then, the washing solution and the mixed solution were combined. The mixture was stirred for 30 minutes and made to stand still for 30 minutes, followed by liquid separation. The liquid separation property was very poor. After liquid separation, the organic layer was added with 2.4 kg of activated carbon and 720 kg of 10% saline water, and then the mixture was stirred for 30 minutes. The resultant solution was filtered off with a filtration device precoated with 6.7 kg of radiolite, activated carbon was washed with 43.2 kg of ethyl acetate, and the obtained filtrate and the washing solution were combined and stirred, and then made to stand still for 30 minutes, followed by liquid separation. The liquid separation speed calculated in the same manner as in Example 1 was 0.1 m/hr. After the aqueous layer was separated, the organic layer was washed with 720 kg of 10% saline water and made to stand still, followed by liquid separation. The liquid separation speed calculated in the same manner as in Example 1 was 0.1 m/hr or less.

The organic layer was charged with 493.7 kg of chlorobenzene, and ethyl acetate, 594.6 kg of chlorobenzene, and 6.5 kg of γ-alumina were charged therein by vacuum concentration, and the mixture was stirred at 80° C. for 30 minutes. After filtration at the same temperature, alumina was washed with 32.2 kg of chlorobenzene and added to the reaction solution. After 583.4 kg of chlorobenzene was distilled out by filtration under reduced pressure, the residual solution was cooled to 20° C. and stirred at 15 to 20° C. for 1 hour. Crystals were separated by filtration and washed with 159.3 kg of a chlorobenzene solution dissolved with 0.73 kg of dibutylhydroxytoluene to give 79.0 kg of wet crystals. After drying the crystals under reduced pressure, 59.6 kg of N-methacryloyl-4-cyano-3-trifluoromethylaniline was obtained. The LC surface percentage was 99.95%, and the yield was 90.8%.

Reference Example 5

A reaction container was charged with 85.5 kg of N,N-dimethylacetamide, 29.5 kg of methacrylic acid, and 0.05 kg of dibutylhydroxytoluene, and the temperature was reduced to −5° C. Thionyl chloride in an amount of 40.8 kg was dropped thereto at −4.1 to −3.9° C. over 4.0 hours, and the reaction solution was kept at −6.9 to −4.1° C. for 1 hour. A solution obtained by dissolving 48.0 kg of commercially available 4-cyano-3-trifluoromethylaniline (LC surface percentage: 99.39%) in 98.9 kg of dimethylacetamide was dropped into the reaction container at −6.9 to −3.0° C. over 6.1 hours. The container for dropping was washed with 13.5 kg of N,N-dimethylacetamide, the washing liquid was added to the reaction solution, and the solution was kept at −4.8 to −3.0° C. for 1 hour. After completion of the reaction, the reaction solution was dropped to a mixed solution of 367.6 kg of ethyl acetate and 336.0 kg of water at 20° C. or less. The container for dropping was washed with 22.5 kg of N,N-dimethylacetamide, the washing liquid was added to the reaction solution, and the pH of the reaction solution was adjusted to 7.0 with 477.6 kg of an aqueous 16% sodium carbonate solution. The resultant solution was stirred for 30 minutes and then made to stand still for 30 minutes, followed by liquid separation. The liquid separation speed calculated in the same manner as in Example 1 was 0.7 m/hr. The organic layer was added with 720 kg of 10% saline water and the resultant solution was stirred for 30 minutes and made to stand still for 30 minutes, followed by liquid separation. The liquid separation speed calculated in the same manner as in Example 1 was 0.1 m/hr.

Industrial Applicability

The present invention provides a method for producing N-methacryloyl-4-cyano-3-trifluoromethylaniline that is a raw material for producing bicalutamide used as an active ingredient of medicaments.

The invention claimed is:

1. A method for producing N-methacryloyl-4-cyano-3-trifluoromethylaniline, wherein 4-cyano-3-trifluoromethylaniline is crystallized from a mixed solvent of methanol and water, and the obtained 4-cyano-3-trifluoromethylaniline is reacted with methacryloyl chloride, and wherein a 4-cyano-3-trifluoromethylaniline solution is treated with activated carbon when 4-cyano-3-trifluoromethylaniline is crystallized from the mixed solvent of methanol and water.

2. The method for producing N-methacryloyl-4-cyano-3-trifluoromethylaniline according to claim 1, wherein methanol and water are used at the rates of 5 to 7 L and 3 to 5 L, respectively, per 1 kg of 4-cyano-3-trifluoromethylaniline when 4-cyano-3-trifluoromethylaniline is crystallized from the mixed solvent of methanol and water.

3. The method for producing N-methacryloyl-4-cyano-3-trifluoromethylaniline according to claim 1, wherein a reaction solvent of 4-cyano-3-trifluoromethylaniline and methacryloyl chloride is N,N-dimethylacetamide.

* * * * *